(12) United States Patent
Serizawa et al.

(10) Patent No.: US 8,580,740 B2
(45) Date of Patent: Nov. 12, 2013

(54) BONE RESORPTION INHIBITORY FOOD MATERIAL FOR INHIBITING BONE RESORPTION

(75) Inventors: Atsushi Serizawa, Saitama (JP); Yoshikazu Morita, Saitama (JP); Daisuke Uetsuji, Saitama (JP); Aiko Ono, Saitama (JP); Hiroaki Matsuyama, Saitama (JP); Satoshi Higurashi, Saitama (JP)

(73) Assignee: Megmilk Snow Brand Co., Ltd., Sapporo (JP)

(*) Notice: Subject to any disclaimer, the term of this patent is extended or adjusted under 35 U.S.C. 154(b) by 0 days.

(21) Appl. No.: 12/740,711

(22) PCT Filed: Oct. 28, 2008

(86) PCT No.: PCT/JP2008/003066
§ 371 (c)(1),
(2), (4) Date: Jul. 1, 2010

(87) PCT Pub. No.: WO2009/057282
PCT Pub. Date: May 7, 2009

(65) Prior Publication Data
US 2010/0261883 A1     Oct. 14, 2010

(30) Foreign Application Priority Data
Nov. 1, 2007   (JP) .................. 2007-285408

(51) Int. Cl.
*A61K 38/00* (2006.01)
*C07K 14/00* (2006.01)

(52) U.S. Cl.
USPC ........................................ 514/16.7; 530/350

(58) Field of Classification Search
None
See application file for complete search history.

(56) References Cited

U.S. PATENT DOCUMENTS

| | | | |
|---|---|---|---|
| 4,667,018 A | 5/1987 | Prieels et al. | |
| 4,946,944 A | 8/1990 | Frankinet et al. | |
| 4,997,914 A | 3/1991 | Kawakami et al. | |
| 5,932,259 A | 8/1999 | Kato et al. | |
| 6,607,743 B1* | 8/2003 | Yoshioka et al. | 424/439 |
| 6,649,590 B2* | 11/2003 | Takada et al. | 514/16.9 |
| 2003/0013661 A1 | 1/2003 | Takada et al. | |
| 2006/0228345 A1 | 10/2006 | Motouri et al. | |
| 2010/0234296 A1 | 9/2010 | Serizawa et al. | |

FOREIGN PATENT DOCUMENTS

| | | |
|---|---|---|
| EP | 0556083 | 8/1993 |
| JP | 61-246198 | 11/1986 |
| JP | 63-255300 | 10/1988 |
| JP | 64-86839 | 3/1989 |
| JP | 5-202098 | 8/1993 |
| JP | 5-320066 | 12/1993 |
| JP | 08-151331 | 6/1996 |
| JP | 10-007585 | 1/1998 |
| JP | 3092874 | 9/2000 |
| JP | 3112637 | 11/2000 |
| JP | 3160862 | 4/2001 |
| JP | 2001-346519 | 12/2001 |
| JP | 2004-115509 | 4/2004 |
| JP | 2004-331556 | * 11/2004 |
| JP | 2005-060321 | 3/2005 |

OTHER PUBLICATIONS

Matsuoka et al. "Cystatin C in Milk Basic Protein (MBP) and Its Inhibitory Effect on Bone Resorption", Biosci. Biotechnol. Biochem., 2002, 66(12):2531-2536.*
Maes et al., "The complete amino acid sequence of bovine milk angiogenin", Febs Lett., 1998, 241(1-2):41-45.*
Morita et al., "Identification of angiogenin as the osteoclastic bone resorption-inhibitory factor in bovine milk", Bone 42 (2008) 380-387—(Available online Oct. 4, 2007).*
English Machine Translation of JP 2004-331556 (Nov. 2004).*
U.S. Appl. No. 12/740,709 to Atsushi Serizawa et al., which application is the National Stage of PCT/JP2008/003064 filed Oct. 28, 2008.
U.S. Appl. No. 12/740,752 to Atsushi Serizawa et al., which application is the National Stage of PCT/JP2008/003065 filed Oct. 28, 2008.
English language Abstract of JP 4-183371, corresponding to JP 3160862, Apr. 25, 2001.
English language Abstract of JP 5-176715, corresponding to JP 3092874, Sep. 25, 2000.
International Search Report that issued with respect to PCT/JP2008/003066, mailed Dec. 2, 2008.
International Preliminary Report on Patentability, including the Written Opinion (in English) for PCT/JP2008/003066, mailed Jun. 10, 2010.

* cited by examiner

*Primary Examiner* — Suzanne M Noakes
(74) *Attorney, Agent, or Firm* — Greenblum & Bernstein, P.L.C.

(57) ABSTRACT

A milk protein fraction having following properties (1) to (4) is excellent in bone resorption inhibitory effect, and is useful for preventing or treating bone diseases:

(1) the milk protein fraction is derived from milk;
(2) the milk protein fraction is a fraction containing a protein having a molecular weight of 12,000 to 16,000 Daltons;
(3) the milk protein fraction has a basic amino acid content of 18 to 20 wt % in the constitutional amino acid composition, and the ratio of the amount of a basic amino acid(s) to the amount of an acidic amino acid(s) is 0.7 to 0.9; and
(4) the milk protein fraction has a bone resorption inhibitory effect.

11 Claims, 1 Drawing Sheet

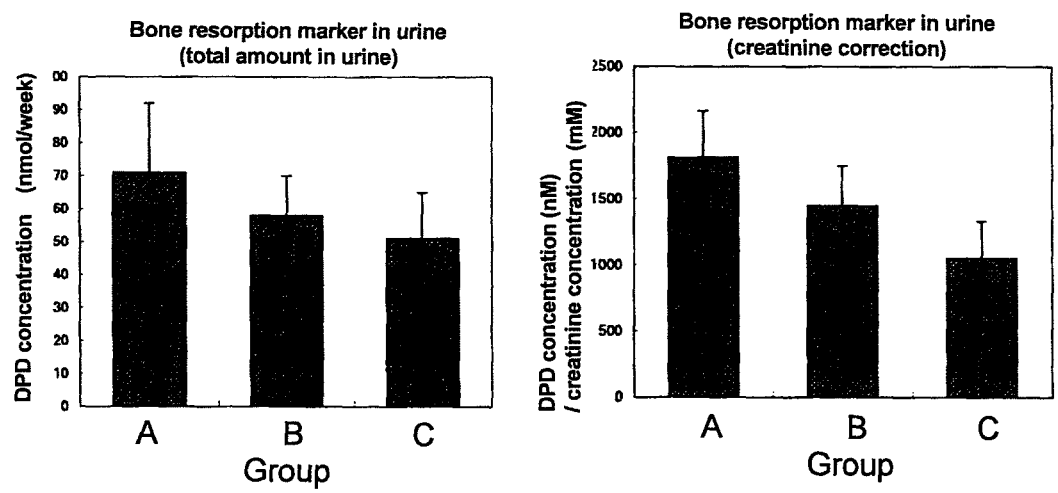

BONE RESORPTION INHIBITORY FOOD MATERIAL FOR INHIBITING BONE RESORPTION

TECHNICAL FIELD

The present invention relates to a milk protein fraction or a milk protein fraction degradation product that exhibits a bone resorption inhibitory effect.

Since the milk protein fraction or the milk protein fraction degradation product according to the present invention exhibits a bone resorption inhibitory effect, the milk protein fraction or the milk protein fraction degradation product is useful as a bone resorption inhibitory agent that aims at preventing or treating bone diseases or strengthening a bone, and is also useful as an active ingredient of a pharmaceutical, food, drink, or feed that aims at preventing or treating bone diseases or strengthening a bone.

BACKGROUND ART

In recent years, various bone diseases, such as osteoporosis, bone fractures, lumbago or the like have increased along with the progressive increase in the elderly population. In a bone tissue, osteogenesis and bone resorption incessantly occur. In a young person, a balance between osteogenesis and bone resorption is kept, but the balance is disrupted to bone resorption owing to various causes with aging (uncoupling). Continuance of this state for a long period of time makes the bone tissue fragile, resulting in occurrence of various bone diseases, such as osteoporosis, bone fractures, and lumbago. It is considered that prevention of the uncoupling enables prevention of various bone diseases, such as osteoporosis, bone fractures, and lumbago.

Conventionally, in order to prevent the uncoupling to prevent or treat bone diseases, the following methods have been performed: (1) calcium supplementation by diet, (2) light exercise, (3) insolation, (4) medication, and the like. For calcium supplementation by diet, there are used calcium salts, such as calcium carbonate, calcium phosphate or the like, or natural calcium agents, such as eggshell, fish bone powder or the like. However, these materials are not necessarily suitable for oral intake. Jogging, walking, or the like may be recommended as light exercise. However, even light exercise is troublesome for a person whose body has weakened, and it is almost impossible for a bedridden old person to do exercise. It is considered that insolation is a good means to supplement activated vitamin $D_3$, but it is not sufficient in itself. 1α-Hydroxyvitamin $D_3$, a calcitonin preparation, or the like is used for administration of a pharmaceutical, and is known to be effective for treating osteoporosis. However, these substances are pharmaceuticals themselves and cannot be used as a food material.

The inventors of the present invention have searched for a bone-strengthening factor contained in milk in order to obtain a bone-strengthening substance that can be used as a food material. As a result, the inventors found that a protein and a peptide mixture obtained by removing a salt derived from a milk serum from a water-soluble fraction of a milk serum protein exhibit a bone-strengthening effect (see Patent Document 1, for example). The inventors found that a fraction obtained by subjecting an aqueous solution of the protein and the peptide mixture to an ethanol treatment, a heat treatment, a salting treatment, and an ultrafiltration membrane treatment exhibits an osteoblast growth promoting effect and a bone-strengthening effect (see Patent Documents 2 and 3, for example). The inventors further found that a basic protein contained in milk exhibits an osteoblast growth promoting effect, a bone-strengthening effect, and a bone resorption prevention effect (see Patent Document 4, for example).

Patent Document 1: Japanese Patent No. 3160862
Patent Document 2: Japanese Patent No. 3092874
Patent Document 3: JP-A-H05-320066
Patent Document 4: Japanese Patent No. 3112637

DISCLOSURE OF THE INVENTION

Problems to be Solved by the Invention

An object of the present invention is to provide a milk protein fraction or a milk protein fraction degradation product that exhibits a bone resorption inhibitory effect and can be used as a food material, a bone resorption inhibitory agent containing the milk protein fraction or the milk protein fraction degradation product that exhibits a bone resorption inhibitory effect, and a pharmaceutical, food, drink, or feed containing the milk protein fraction or the milk protein fraction degradation product that exhibits a bone resorption inhibitory effect.

Means for Solving the Problems

The inventors searched for a novel bone resorption inhibitory material, and found that a fraction exhibiting a high bone resorption inhibitory effect as compared with a known food material could be obtained. Based on those findings, the inventors thus obtained a bone resorption inhibitory agent containing the milk protein fraction or the milk protein fraction degradation product that exhibits a bone resorption inhibitory effect, and a pharmaceutical, food, drink, or feed containing the milk protein fraction or the milk protein fraction degradation product that exhibits a bone resorption inhibitory effect.

Specifically, the present invention is constituted as follows:
(A) A milk protein fraction characterized in that
 (1) the milk protein fraction is derived from milk,
 (2) the milk protein fraction contains proteins having a molecular weight of 12,000 to 16,000 daltons determined by sodium dodecyl sulfate-polyacrylamide gel electrophoresis (SDS-PAGE),
 (3) the milk protein fraction contains 18 to 20 wt % of basic amino acids in the constituent amino acid composition, and has a basic amino acid/acidic amino acid ratio of 0.7 to 0.9, and
 (4) the milk protein fraction has a bone resorption inhibitory effect.
(B) A milk protein fraction degradation product obtained by degrading the above milk protein fraction with a protease.
(C) A bone resorption inhibitory agent comprising the milk protein fraction or the milk protein fraction degradation product according to (A) or (B), respectively.
(D) A bone resorption inhibitory pharmaceutical comprising the milk protein fraction or the milk protein fraction degradation product according to (A) or (B), respectively.
(E) A bone resorption inhibitory food or drink comprising the milk protein fraction or the milk protein fraction degradation product according to (A) or (B), respectively.
(F) A bone resorption inhibitory feed comprising the milk protein fraction or the milk protein fraction degradation product according to (A) or (B), respectively.

Effects of the Invention

The bone resorption inhibitory agent containing the milk protein fraction or the milk protein fraction degradation product that exhibits a bone resorption inhibitory effect as an active ingredient, and the bone resorption inhibitory pharmaceutical, food, drink, or feed containing the milk protein fraction or the milk protein fraction degradation product that exhibits a bone resorption inhibitory effect according to the present invention inhibit bone resorption in a body when taken orally.

Therefore, the bone resorption inhibitory agent containing the milk protein fraction or the milk protein fraction degradation product that exhibits a bone resorption inhibitory effect as an active ingredient, and the bone resorption inhibitory pharmaceutical, food, drink, or feed containing the milk protein fraction or the milk protein fraction degradation product that exhibits a bone resorption inhibitory effect according to the present invention exhibit a bone-strengthening effect by inhibiting bone resorption in the body of a human or an animal, and are effective for suppressing a decrease in bone mass due to osteoporosis or the like.

BRIEF DESCRIPTION OF THE DRAWINGS

FIG. 1 shows the measurement results of the total amount of deoxypyridinoline (DPD) (which is a bone resorption marker in urine) in urine and the DPD concentration per creatinine (Test Example 2).

BEST MODE FOR CARRYING OUT THE INVENTION

The present invention relates to a bone resorption inhibitory agent including a milk protein fraction or a milk protein fraction degradation product that exhibits a bone resorption inhibitory effect as an active ingredient, as well as a bone resorption inhibitory pharmaceutical, food or drink, and feed including a milk protein fraction or a milk protein fraction degradation product that exhibits a bone resorption inhibitory effect.

The milk protein fraction according to the present invention that exhibits a bone resorption inhibitory effect, for example, is brought a milk raw material, such as skim milk, milk serum or the like into contact with a cation-exchange resin, and the cation-exchange resin is washed with 0.3 M sodium chloride solution, and then the milk protein adsorbed on the cation-exchange resin may be eluted using a 0.6M sodium chloride eluant. Note that salt such as a potassium salt, an ammonium salt, a phosphate, an acetate, a carbonate, or the like may be also used in addition to sodium chloride. The milk protein fraction according to the present invention may be obtained by appropriately adjusting the ionic strength of the washing agent to 0.3 to 0.4 and the ionic strength of the elution solution to 0.55 to 0.65. Furthermore, the milk protein fraction according to the present invention may be obtained by collecting the eluted fraction, desalting and concentrating the fraction using a reverse osmosis (RO) membrane, electrodialysis (ED), or the like, and optionally drying the resulting product. Examples of the reverse osmosis (RO) membrane include Desal-3 (manufactured by Desalination), HR-95 (manufactured by Dow Danmark), NTR-729HF (manufactured by Nitto Denko Corporation), and the like. Examples of an electrodialysis (ED) system include electrodialysis systems manufactured by Yuasa-Ionics Inc. and Nippon Rensui Co., Ltd.

As a method of obtaining a trace protein fraction derived from milk, a method of obtaining a protein fraction by bringing milk or a raw material derived from milk into contact with a cation exchanger, and eluting the basic protein fraction that is adsorbed on the cation exchanger using an eluant that has a pH of more than 5 and an ionic strength of more than 0.5 (JP-A-H05-202098), a method of obtaining a protein fraction using an alginic acid gel (JP-A-S61-246198), a method of obtaining a protein fraction from a milk serum using porous inorganic particles (JP-A-H01-86839), a method of obtaining a protein fraction from milk using a sulfated ester compound (JP-A-S63-255300), and the like have been known. Protein fractions obtained by those methods may be used as the protein fraction that is derived from milk and exhibits a bone resorption inhibitory effect according to the present invention. In the present invention protein fractions may be obtained by those methods.

The milk protein fraction thus collected may be normally powdered by freeze-drying or the like before use.

The milk protein fraction that exhibits a bone resorption inhibitory effect used in the present invention preferably contains 18 to 20 wt % of basic amino acids in the constituent amino acid composition, and has a basic amino acid/acidic amino acid ratio of 0.7 to 0.9. The effect of the present invention may not be achieved if the content of basic amino acids or the basic amino acid/acidic amino acid ratio is outside the above range. The milk protein fraction according to the present invention is a mixture of various proteins having a molecular weight of 12,000 to 16,000 daltons and an isoelectric point of 10 or more.

The milk protein fraction degradation product has the same amino acid composition as that of the milk protein fraction. For example, a milk protein fraction degradation product having an average molecular weight of 4000 or less may be obtained by treating a milk protein fraction obtained by the above method with a protease such as pepsin, trypsin, chymotrypsin or the like, and optionally treating the resulting product with a protease such as pancreatin or the like. The milk protein fraction degradation product is normally powdered by freeze-drying or the like before use.

As milk or a raw material derived from milk which can be used as source of the milk protein fraction according to the present invention that exhibits a bone resorption inhibitory effect, cow milk, human milk, goat milk, ewe milk or the like may be given. Such milks may be used as is, or recombined milk, skim milk, whey, or the like derived from such milks may be used.

The milk protein fraction or the milk protein fraction degradation product that exhibits a bone resorption inhibitory effect and is an active ingredient may be used as is when administering the bone resorption inhibitory agent according to the present invention. Note that it is also possible to use after being formulated into a powdered pharmaceutical, granules, a tablet, a capsule, a drinkable preparation, or the like in accordance with a conventional method. Moreover, the milk protein fraction or the milk protein fraction degradation product, as is or after formulating a preparation thereof, may be added to a nutrient preparation, food and drink, or the like to achieve a bone resorption inhibitory effect. Since the milk protein fraction or the milk protein fraction degradation product according to the present invention is relatively stable against heat, the milk protein fraction or the milk protein fraction degradation product can be heat-sterilized under conventional conditions.

In the present invention, in order to achieve a bone resorption inhibitory effect the dosage or the like may be appropriately determined taking account of weight, sex, age, and the like. The milk protein fraction or the milk protein fraction degradation product may be adjusted the formulating amount thereof so that a normal adult takes the milk protein fraction or the milk protein fraction degradation of the present invention in an amount of 1 to 50 mg/day. That is, the milk protein fraction or the milk protein fraction degradation product according to the present invention is effective at a low dosage. In the present invention, the ingredient having a bone resorption inhibitory effect exerts the bone resorption inhibitory effect when orally administered a bone resorption inhibitory agent or a pharmaceutical, food and drink, or feed formulated the bone resorption inhibitory agent The present invention is further described below by way of reference examples, examples, and test examples. Note that the following examples merely illustrate several aspects of the present invention, and should not be construed as limiting the present invention.

Reference Example 1

A milk protein fraction exhibiting a bone resorption inhibitory effect which was commercially available was prepared in accordance with the following method (see Japanese Patent No. 3112637).

A column (diameter: 10 cm) loaded with 0.5 litters of sulfonated Chitopearl (cation-exchange resin; manufactured by Fuji Spinning Co., Ltd.) was sufficiently washed with deionized water. After passing 50 l of unsterilized skim milk through the column at a flow rate of 100 ml/min, the column was sufficiently washed with deionized water. 2.5 l of a 0.05M phosphate buffer (pH 7.0) containing 0.95M sodium chloride was then passed through the column to elute proteins adsorbed on the resin. The eluate was desalted and concentrated by means of a reverse osmosis (RO) membrane treatment, and then freeze-dried to obtain a powdery milk protein fraction. The above procedure was repeated twice to obtain 104 g of a protein fraction. The protein fraction had an isoelectric point of 7.0 to 8.5. The content of basic amino acids in the protein fraction was 17.8%.

Example 1

A column (diameter: 10 cm) loaded with 0.5 l of sulfonated Chitopearl (cation-exchange resin; manufactured by Fuji Spinning Co., Ltd.) was sufficiently washed with deionized water. After passing 50 l of unsterilized skim milk through the column at a flow rate of 100 nil/min, the column was sufficiently washed with a 0.05M phosphate buffer (pH 7.0) containing 0.3M sodium chloride. 2.5 l of a 0.05M phosphate buffer (pH 7.0) containing 0.55M sodium chloride was then passed through the column to elute proteins adsorbed on the resin. The eluate was desalted and concentrated by means of a reverse osmosis (RO) membrane treatment, and then freeze-dried to obtain a powdery milk protein fraction. The above procedure was repeated five times to obtain 37.4 g of a protein fraction. The protein fraction had a molecular weight of 12,000 to 16,000 daltons and an isoelectric point of 10 or more. The content of basic amino acids in the constituent amino acid contained in the protein fraction was 18 to 20%. The protein fraction had a basic amino acid/acidic amino acid ratio of 0.7 to 0.9.

Example 2

A column (diameter: 10 cm) loaded with 0.5 l of sulfonated Chitopearl (cation-exchange resin; manufactured by Fuji Spinning Co., Ltd.) was sufficiently washed with deionized water. After passing 50 l of unsterilized skim milk through the column at a flow rate of 100 ml/min, the column was sufficiently washed with a 0.05M phosphate buffer (pH 7.0) containing 0.4M sodium chloride. 2.5 l of a 0.05M phosphate buffer (pH 7.0) containing 0.65M sodium chloride was then passed through the column to elute proteins adsorbed on the resin. The eluate was desalted and concentrated by means of a reverse osmosis (RO) membrane treatment, and then freeze-dried to obtain a powdery milk protein fraction. The above procedure was repeated three times to obtain 22.8 g of a protein fraction. The protein fraction had a molecular weight of 12,000 to 16,000 daltons and an isoelectric point of 10 or more. The content of basic amino acids in the constituent amino acid contained in the protein fraction was 18 to 20%. The protein fraction had a basic amino acid/acidic amino acid ratio of 0.7 to 0.9.

Example 3

37.4 g of the milk protein fraction obtained in Example 1 was dissolved in 10 l of distilled water. After adding pepsin (manufactured by Kanto Kagaku Co., Ltd.) so as to be the concentration of 2%, the milk protein fraction was hydrolyzed at 37° C. for one hour with stirring. After the mixture was neutralized to pH 6.8 with a sodium hydroxide solution, 1% pancreatin (manufactured by Sigma) was added thereto. The mixture was then reacted at 37° C. for two hours. After completion of the reaction, the protease was inactivated by heating the mixture at 80° C. for 10 minutes to obtain 36.2 of a milk protein fraction degradation product.

Example 4

22.8 g of the milk protein fraction obtained in Example 2 was dissolved in 8 l of distilled water. After adding trypsin (manufactured by Kanto Kagaku Co., Ltd.) so as to be the concentration of 2%, the milk protein fraction was hydrolyzed at 37° C. for one hour with stirring. After the mixture was neutralized to pH 6.6 with a sodium hydroxide solution, 1% pancreatin (manufactured by Sigma) was added thereto. The mixture was then reacted at 37° C. for two hours. After completion of the reaction, the protease was inactivated by heating the mixture at 80° C. for 10 minutes to obtain 21.1 g of a milk protein fraction degradation product.

Test Example 1

The bone resorption inhibitory effect of the protein fractions obtained in Reference Example 1 and Example 1 was determined in accordance with the method proposed by Takada et al. (Y. Takada et al., Bone and Mineral, vol. 17, pp. 347-359, 1992). The long bone was removed from an ICR mouse (10 to 20-day-old). After removing soft tissues, the bone was mechanically ground in an α-MEM solution containing 5% fetal bovine serum to obtain total marrow cells containing osteoclasts. The cells (about $2 \times 10^6$ cells) were spotted on an ivory piece using an α-MEM solution containing 5% fetal bovine serum. After several hours, an α-MEM solution containing 5% fetal bovine serum to which the sample was added, was added to the cells. The cells were cultured for five days, and the bone resorption activity of the osteoclasts was determined. Specifically, the bone resorption activity was evaluated by removing the cultured cells from the ivory piece, stained with hematoxylin, and measuring the bone resorption pit area by image analysis. The ratio of the area of the pit in each sample with respect to the area of the pit in a control (blank) was provided as the bone resorption activity, and indicated by percentage (%). The results are shown in Table 1.

TABLE 1

| Sample | Final concentration | bone resorption activity |
| --- | --- | --- |
| Control | — | 100 |
| Milk protein fraction (Reference example 1) | 0.01 mg/ml | 75.2 ± 3.7 (%, ±SD) |
| Milk protein fraction (Example 1) | 0.01 mg/ml | 10.9 ± 4.7 |
| Milk protein fraction (Example 1) | 0.001 mg/ml | 22.3 ± 5.6 |

The milk protein fraction according to the present invention (Example 1) showed a significant bone resorption inhibitory effect as compared with the control and the milk protein fraction obtained in Reference Example 1.

Test Example 2

The bone resorption inhibitory effect of the milk protein fractions obtained in Reference Example 1 and Example 1 was determined by animal experiments. Wistar rats (female, six-week-old) were used for the animal experiments. After preliminary feeding for one week, the ovary was removed from each rat. Low calcium food (calcium content: 0.3%) was then fed to the rats for five weeks. After a recovery period, the rats were subjected to the animal experiments. The rats from which the ovary was removed and which were fed the low calcium food (AIN-76 base) for five weeks obviously had osteoporosis. The rats having osteoporosis were divided into three test groups (eight mice/each group) of a control group (Group A) that was not administered a milk protein fraction, a group (Group B) that was administered 0.1 wt % of the milk protein fraction obtained in Reference Example 1, and a group (Group C) that was administered 0.1 wt % of the milk protein fraction obtained in Example 1. A test feed shown in Table 2 was fed to each group for four months. The nitrogen content in each test feed was equally adjusted to 17.06% using casein.

TABLE 2

| | Group | | |
| --- | --- | --- | --- |
| | A | B | C |
| Casein | 20.0 | 19.9 | 19.9 |
| Cornstarch | 15.0 | 15.0 | 15.0 |
| Cellulose | 5.0 | 5.0 | 5.0 |
| Corn oil | 5.0 | 5.0 | 5.0 |
| Vitamin mix | 1.0 | 1.0 | 1.0 |
| Mineral mix (including no calcium) | 3.5 | 3.5 | 3.5 |
| $CaHPO_4 \cdot 2H_2O$ | 1.29 | 1.29 | 1.29 |
| Sucrose | 48.91 | 48.91 | 48.91 |
| DL-methionine | 0.3 | 0.3 | 0.3 |
| Milk protein fraction obtained in Reference example 1 | — | 0.1 | — |
| Milk protein fraction obtained in Example 1 | — | — | 0.1 |

(wt %)

The rats that were fed for four months were fed in a metabolic cage over the last one week, and urine was collected. The content of deoxypyridinoline (DPD; which is a bone resorption marker existing in urine) in urine was measured using an Osteolinks "DPD" (manufactured by Sumitomo Seiyaku Biomedical Co., Ltd.). A more accurate DPD amount can be calculated as a bone resorption marker that is independent of the amount of urine if correcting the DPD concentration using the concentration of creatinine of which the excretion amount per day does not vary depending on the amount of urine. Therefore, the creatinine concentration in urine was measured using a Creatinine Test Wako (manufactured by Wako Pure Chemical Industries, Ltd.), and the accurate DPD amount was corrected through calculating the DPD concentration per creatinine. FIG. 1 shows the measurement results for the total deoxypyridinoline (DPD, which is a bone resorption marker in urine) amount in urine and the DPD concentration per creatinine when four months had elapsed from the commencement of administration. As shown in FIG. 1, the total DPD amount for one week and the DPD concentration after creatinine correction of the group (Group B) that was administered the milk protein fraction obtained in Reference Example 1 and the groups (Groups C) that were administered the milk protein fraction obtained in Example 1 were lower than those of the control group (Group A) that was administered no milk protein fraction. The milk protein fraction obtained in Reference Example 1 also showed a bone resorption inhibitory effect. However, it became obvious that the present invention product exhibited a higher bone resorption inhibitory effect as compared with Reference Example 1.

Similar effects were observed when using the hydrolyzed milk protein fractions obtained in Examples 3 and 4, but not shown the experimental results.

Example 5

100 mg of the milk protein fraction obtained in Example 1 was added with 93.4 g of crystalline glucose hydrate, 5 g of calcium carbonate, 1 g of a sugar ester, and 0.5 g of flavor, and mixed. The resultant was then formed into a tablet to obtain a bone resorption inhibitory agent according to the present invention.

Example 6

The components were mixed in accordance with the composition shown in Table 3 to obtain a dough. The dough was formed and baked to produce a cookie for inhibiting a bone resorption.

TABLE 3

| Flour | 50.0 (wt %) |
| --- | --- |
| Sugar | 20.0 |
| Salt | 0.5 |
| Margarine | 12.5 |
| Egg | 12.1 |
| Water | 4.0 |
| Sodium hydrogen carbonate | 0.1 |
| Ammonium bicarbonate | 0.2 |
| Calcium carbonate | 0.5 |
| Milk protein fraction powder (Example 1) | 0.1 |

Example 7

A bone resorption inhibitory fruit juice drink having a composition shown in Table 4 was produced.

TABLE 4

| Isomerized sugar mix | 15.0 (wt %) |
| --- | --- |
| Fruit juice | 10.0 |
| Citric acid | 0.5 |
| Milk protein fraction powder (Example 1) | 0.5 |
| Flavor | 0.1 |
| Calcium | 0.1 |
| Water | 73.8 |

Example 8

The ingredients were mixed in accordance with the formulation shown in Table 4 to produce a bone resorption inhibitory dog food.

TABLE 5

| | |
|---|---|
| Milk protein fraction powder (Example 1) | 2.5 (wt %) |
| Skim milk powder | 13.5 |
| Soybean cake | 12.0 |
| Soybean oil | 4.0 |
| Corn oil | 2.0 |
| Palm oil | 27.0 |
| Corn starch | 14.0 |
| Flour | 9.0 |
| Bran | 2.0 |
| Vitamin mix | 9.0 |
| Mineral mix | 2.0 |
| Cellulose | 3.0 |

Example 9

Each ingredient was mixed in accordance with the formulation shown in Table 6, and formed under pressure to produce a bone resorption inhibitory tablet containing the milk protein fraction degradation product obtained in Example 3.

TABLE 6

| | |
|---|---|
| Crystalline glucose hydrate | 59.4 (wt %) |
| Milk protein fraction degradation product (Example 3) | 16.0 |
| Corn starch | 12.0 |
| Cellulose | 4.0 |
| Corn oil | 4.0 |
| Vitamin mix (including choline) | 1.0 |
| Mineral mix | 3.6 |

Example 10

Each ingredient was mixed in accordance with the formulation shown in Table 7, and emulsified at 85° C. to produce a bone resorption inhibitory processed cheese containing the milk protein fraction degradation product obtained in Example 4.

TABLE 7

| | |
|---|---|
| Gouda cheese | 43.0 (wt %) |
| Cheddar cheese | 43.0 |
| Sodium citrate | 2.0 |
| Milk protein fraction degradation product (Example 4) | 0.5 |
| Calcium derived from milk | 1.0 |
| Water | 10.5 |

INDUSTRIAL APPLICABILITY

Since the milk protein fraction or milk protein fraction degradation product according to the present invention exhibits a bone resorption inhibitory effect, and is effective for suppressing a decrease in bone mass due to osteoporosis or the like, the milk protein fraction or milk protein fraction degradation product may be useful as a bone resorption inhibitory agent comprising the milk protein fraction or milk protein fraction degradation product that exhibits a bone resorption inhibitory effect as an active ingredient, and a bone resorption inhibitory pharmaceutical, food, drink, or feed containing the milk protein fraction or the milk protein fraction degradation product that exhibits a bone resorption inhibitory effect that exhibits a bone resorption inhibitory effect.

The invention claimed is:

1. A milk protein fraction having following characteristics (1) to (5):
   (1) the milk protein fraction is derived from milk,
   (2) the milk protein fraction contains proteins having a molecular weight of 12,000 to 16,000 daltons determined by sodium dodecyl sulfate-polyacrylamide gel electrophoresis (SDS-PAGE),
   (3) the milk protein fraction contains 18 to 20 percent of basic amino acids by weight of the constituent amino acid composition, and has a basic amino acid/acidic amino acid ratio of 0.7 to 0.9,
   (4) the milk protein fraction has a bone resorption inhibitory effect, and
   (5) the milk protein fraction has an isoelectric point of 10 or more.

2. A milk protein fraction degradation product obtained by degrading the milk protein fraction according to claim 1 with at least one of pepsin, trypsin, or pancreatin.

3. A bone resorption inhibitory agent comprising the milk protein fraction according to claim 1.

4. A bone resorption inhibitory pharmaceutical comprising the milk protein fraction according to claim 1.

5. A bone resorption inhibitory food or drink comprising the milk protein fraction according to claim 1.

6. A bone resorption inhibitory feed comprising the milk protein fraction according to claim 1.

7. A bone resorption inhibitory agent comprising the milk protein fraction degradation product according to claim 2.

8. A bone resorption inhibitory pharmaceutical comprising the milk protein fraction degradation product according to claim 2.

9. A bone resorption inhibitory food or drink comprising the milk protein fraction degradation product according to claim 2.

10. A bone resorption inhibitory feed comprising the milk protein fraction degradation product according to claim 2.

11. A method of inhibiting bone resorption in the body of a human or animal, comprising administering an effective amount of the milk protein fraction of claim 1 to the human or animal.

* * * * *